(12) United States Patent
Johnson et al.

(10) Patent No.: US 9,132,665 B2
(45) Date of Patent: Sep. 15, 2015

(54) SUBSTRATE DEFECT DETECTION MECHANISM

(71) Applicants: Scott Richard Johnson, Erie, CO (US); Harry Reese Lewis, Longmont, CO (US); Casey Ethan Walker, Boulder, CO (US)

(72) Inventors: Scott Richard Johnson, Erie, CO (US); Harry Reese Lewis, Longmont, CO (US); Casey Ethan Walker, Boulder, CO (US)

(73) Assignee: Ricoh Company, Ltd., Tokyo (JP)

( * ) Notice: Subject to any disclaimer, the term of this patent is extended or adjusted under 35 U.S.C. 154(b) by 0 days.

(21) Appl. No.: 13/973,088

(22) Filed: Aug. 22, 2013

(65) Prior Publication Data

US 2015/0054880 A1    Feb. 26, 2015

(51) Int. Cl.
*B41J 29/393*    (2006.01)
*B41J 11/00*    (2006.01)
*G01N 21/89*    (2006.01)
*G01N 21/898*    (2006.01)

(52) U.S. Cl.
CPC ......... *B41J 11/0005* (2013.01); *G01N 21/8903* (2013.01); *G01N 21/8983* (2013.01)

(58) Field of Classification Search
CPC .................................................... B41J 29/393
USPC ............................................................ 347/19
See application file for complete search history.

(56) References Cited

U.S. PATENT DOCUMENTS

| 8,060,234 | B2 | 11/2011 | Hellstrom | |
|---|---|---|---|---|
| 2003/0214648 | A1* | 11/2003 | Rucker et al. | 356/238.1 |
| 2007/0046715 | A1 | 3/2007 | Yamanobe et al. | |
| 2008/0122890 | A1 | 5/2008 | Yorimoto | |
| 2008/0291202 | A1 | 11/2008 | Minhas et al. | |
| 2009/0060316 | A1* | 3/2009 | Ruuska | 382/141 |
| 2010/0091334 | A1* | 4/2010 | Qiao et al. | 358/3.26 |
| 2011/0032337 | A1* | 2/2011 | Rodriguez Ramos et al. | 348/49 |
| 2011/0074860 | A1* | 3/2011 | Saettel et al. | 347/19 |
| 2011/0075193 | A1 | 3/2011 | Kumamoto | |
| 2011/0096342 | A1 | 4/2011 | Burke | |
| 2012/0062634 | A1 | 3/2012 | Obertegger | |
| 2012/0193515 | A1* | 8/2012 | Agranov et al. | 250/208.1 |
| 2013/0016154 | A1* | 1/2013 | Imamura et al. | 347/19 |
| 2013/0163827 | A1* | 6/2013 | Rzadca et al. | 382/112 |

FOREIGN PATENT DOCUMENTS

EP    2244484    10/2010

OTHER PUBLICATIONS

EP Search Report, EP14179284, Feb. 2, 2015, 7 pages.

* cited by examiner

*Primary Examiner* — Geoffrey Mruk
*Assistant Examiner* — Scott A Richmond
(74) *Attorney, Agent, or Firm* — Blakely, Sokoloff, Taylor & Zafman LLP

(57) ABSTRACT

A method is disclosed. The method includes one or more light field cameras recording image data of a substrate during printing to the substrate and a control unit processing the image data received from the one or more light field cameras to identify defect areas in the substrate.

20 Claims, 3 Drawing Sheets

SUBSTRATE DEFECT DETECTION MECHANISM

FIELD OF THE INVENTION

This invention relates generally to the field of printing systems. More particularly, the invention relates to image processing in a printing system.

BACKGROUND

In the high speed print production systems, relatively small variations in substrate (e.g., paper) web alignment, paper movement and surface contour can be critical. The same can be said for a print verification system (PVS) that verifies the print on the back-end of a print production system.

Predictable operations and final quality are affected by attributes such as proper web tension, paper to ink-jet head gap, localized deformity (e.g., cockle), flutter and other mechanical anomalies that affect paper. Various means are currently in use to control and detect these aspects of the print or PVS system. Nonetheless, these mechanisms are static (e.g., tension gauge) or limit sensing (e.g., light beam make/break). The nature of the (paper) web, however, is such that simple edge or threshold sensing is insufficient.

Accordingly, an improved detection mechanism is desired.

SUMMARY

In one embodiment, a method is disclosed. The method includes one or more light field cameras recording image data of a substrate during printing to the substrate and a control unit processing the image data received from the one or more light field cameras to identify defect areas in the substrate.

In a further embodiment, a print system is disclosed. The print system includes a printhead array to apply presentation content to a substrate, one or more light field cameras to record image data of the substrate during application of the printed characters to the substrate and a control unit to process the image data received from the one or more light field cameras to identify defect areas in the substrate.

BRIEF DESCRIPTION OF THE DRAWINGS

A better understanding of the present invention can be obtained from the following detailed description in conjunction with the following drawings, in which.

DETAILED DESCRIPTION

A defective substrate detection mechanism is described. In the following description, for the purposes of explanation, numerous specific details are set forth in order to provide a thorough understanding of the present invention. It will be apparent, however, to one skilled in the art that the present invention may be practiced without some of these specific details. In other instances, well-known structures and devices are shown in block diagram form to avoid obscuring the underlying principles of the present invention.

Reference in the specification to "one embodiment" or "an embodiment" means that a particular feature, structure, or characteristic described in connection with the embodiment is included in at least one embodiment of the invention. The appearances of the phrase "in one embodiment" in various places in the specification are not necessarily all referring to the same embodiment.

Figure 1:
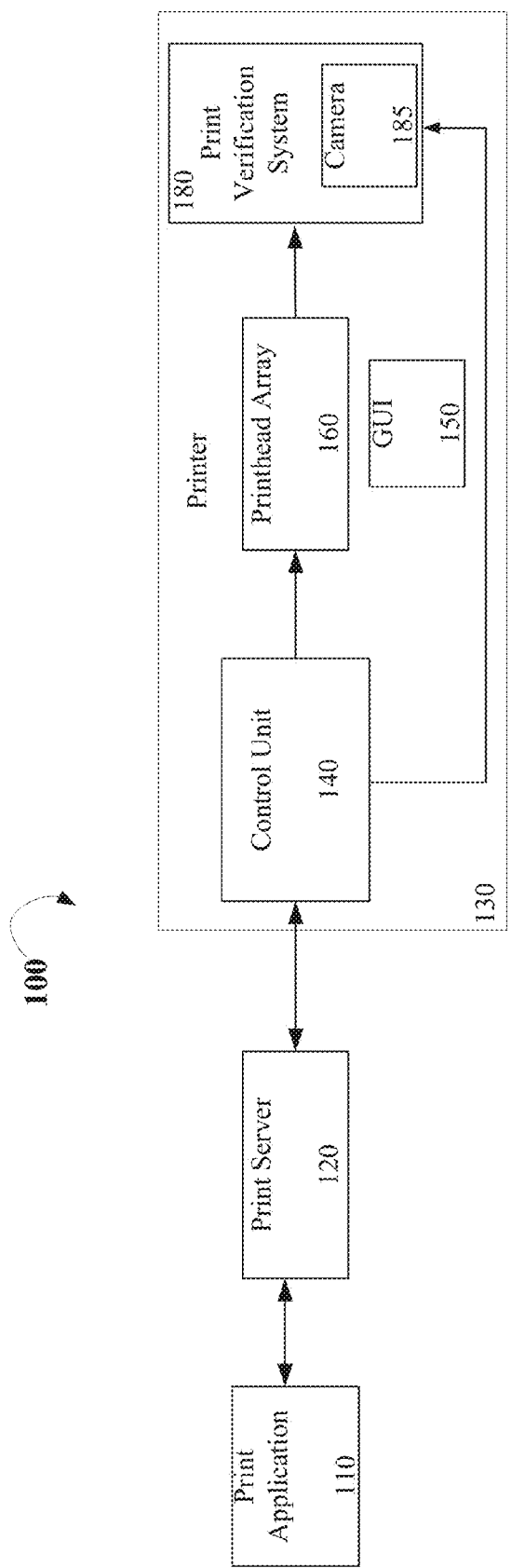
FIG. 1 illustrates one embodiment of a printing system.

FIG. 1 illustrates one embodiment of a printing system 100. Printing system 100 includes a print application 110, a server 120 and a printer 130. Print application 110 makes a request for the printing of a document. In one embodiment, print application 110 provides a print job data stream to print server 120 in a presentation format (e.g., Advanced Function Printing, Portable Document Format (PDF), Post Script, etc.)

Print server 120 processes pages of output that mix all of the elements normally found in presentation documents (e.g., text in typographic fonts, electronic forms, graphics, image, lines, boxes, and bar codes). In one embodiment, the data stream is composed of architected, structured fields that describe each of these elements.

According to one embodiment, printer 130 includes a control unit 140, printhead array 160 and print verification system (PVS) 180. In such an embodiment, print server 120 communicates with control unit 140 in order to integrate with the capabilities and command set of printer 130, and to facilitate interactive dialog between the print server 120 and printer 130. In one embodiment, the dialog between the print server 120 and printer 130 is provided according to a device-dependent bi-directional command/data stream.

Control unit 140 processes and renders objects received from print server 120 and provides sheet maps for printing to printhead array 160. In such an embodiment, control unit 140 includes a multitude (e.g., ten) of compute node machines, with each node having two or more parallel page output handlers (POH's).

PVS 180 is implemented to record mechanical defects in the substrate during printing (e.g., flutter, cockle, wrinkles or z-direction defects), as well as record print quality defects on the substrate. In one embodiment, PVS 180 includes one or more cameras 185. In such an embodiment, cameras 185 are plenoptic cameras that use a microlens array to capture 4D light field information about a scene. Plenoptic cameras may also be referred to as light field cameras. Although described above as being incorporated within PVS 180, other embodiments may feature the plenoptic cameras 185 as standalone units.

According to one embodiment, a camera 185 has the ability to determine focus after image capture. This ability, coupled with the nature of the light source, enables capturing and managing a trans-web profile. Such a profile may be implemented to characterize web distortion (e.g., cockle, flutter, etc.) and periodicity (e.g., oscillation).

Figure 2A:
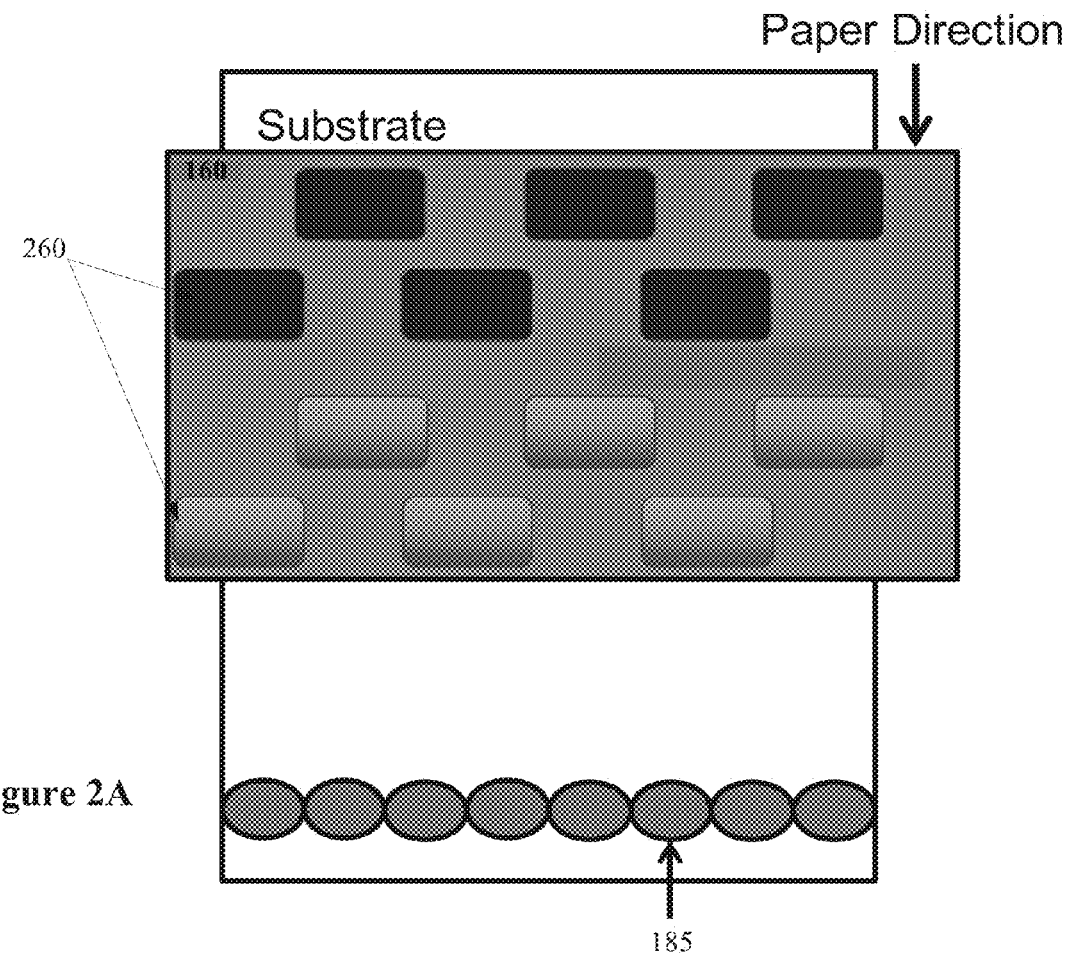
FIGS. 2A and 2B illustrate embodiments of a printer.
Figure 2B:
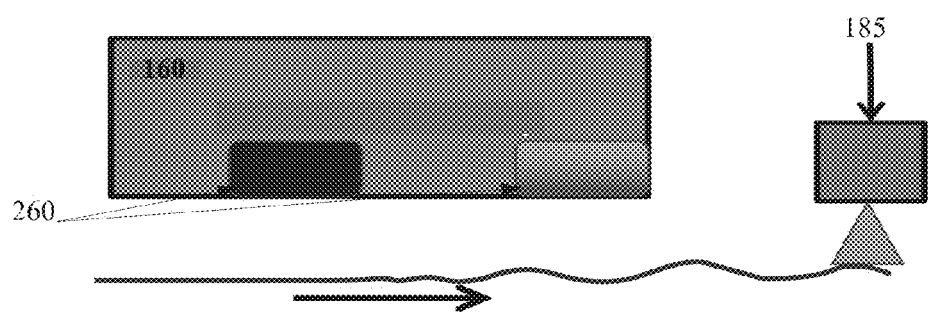

According to one embodiment, one or more plenoptic cameras 185 are installed at strategic points in printer 130 in order to utilize the light-field property to derive measurements. FIG. 2A illustrates one embodiment of a top view of printer 130. As shown in FIG. 2A, printhead array 160 includes printheads 260 that apply presentation content (e.g., printed characters, graphics or other images) via ink (or toner) to a substrate as the substrates passes array 160. The substrate subsequently passes an array of plenoptic cameras 185, which captures images of the substrate. FIG. 2B illustrates one embodiment of a side view of printer 130.

Figure 3A:
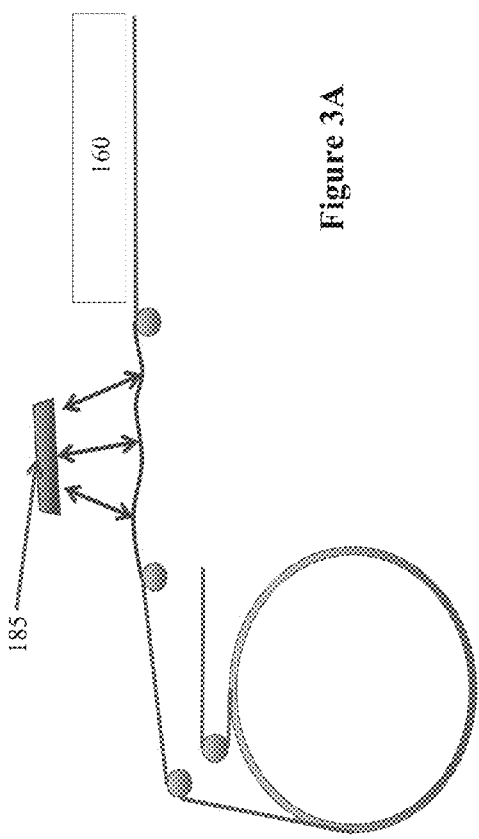
FIGS. 3A and 3B illustrate embodiments of printer substrate path implementations.
Figure 3B:
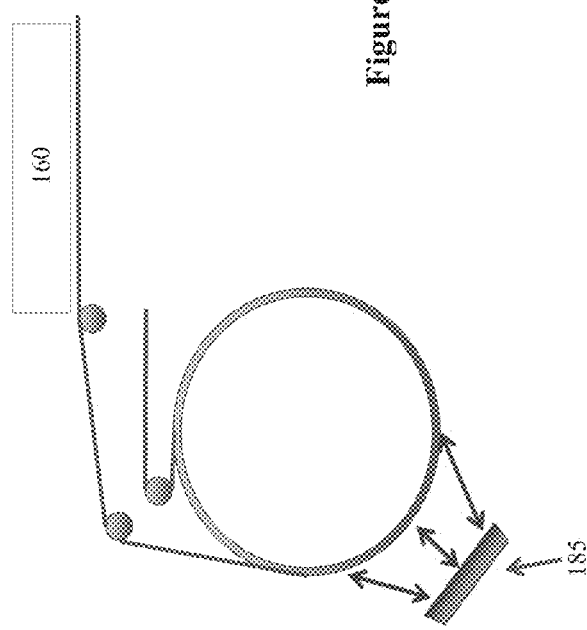

FIG. 3A illustrates one embodiment of a printer substrate path having plenoptic cameras 185 located immediately after the printhead array 160, as shown in FIGS. 2A and 2B. However, FIG. 3B illustrates an embodiment in which plenoptic cameras 185 are located to capture a single image on a radial surface such as a drum or roller. This configuration enables a smaller footprint for print quality verification and reduced image processing requirements.

According to one embodiment, the data collected by plenoptic cameras 185 is transmitted back to control unit 140 for processing to identify mechanical defects in the substrate during printing. However in other embodiments, PVS 180 may include a standalone control unit to perform the processing of the image data.

In one embodiment, control unit 140 may map out the surface of the substrate based on knowledge of the focal lengths of the camera 185 lenses in order to determine the focal length at various points of the substrate. This process provides a three-dimensional (3D) surface of the substrate. In a further embodiment, control unit 140 may focus the captured images of the web and determine, based on a magnitude of variance to get an image into focus, a degree of cockle that has occurred at the web. In another embodiment, control unit 140 may process the images to determine differences in "X" or "Y" direction defects to know whether defect issues are from steering/ rollers or printing/drying.

According to one embodiment, control unit provides dynamic feedback to a paper control system (not shown) within printer 130 to correct defective regions detected during processing the image data. Thus, controller implements the image data to correct paper stability problems, cockling, wrinkling flutter, etc.

In one embodiment, cameras 185 are also implemented to capture color and print quality defects (e.g., jetouts, missing data, etc.). In this embodiment, control unit 140 processes the imaging data to identify such defects. In yet a further embodiment, control unit 140 may transmit a message to a graphical user interface (GUI) 150 at printer 130 to provide defect data to an operator.

Embodiments of the invention may include various steps as set forth above. The steps may be embodied in machine-executable instructions. The instructions can be used to cause a general-purpose or special-purpose processor to perform certain steps. Alternatively, these steps may be performed by specific hardware components that contain hardwired logic for performing the steps, or by any combination of programmed computer components and custom hardware components.

Elements of the present invention may also be provided as a machine-readable medium for storing the machine-executable instructions. The machine-readable medium may include, but is not limited to, floppy diskettes, optical disks, CD-ROMs, and magneto-optical disks, ROMs, RAMs, EPROMs, EEPROMs, magnetic or optical cards, propagation media or other type of media/machine-readable medium suitable for storing electronic instructions. For example, the present invention may be downloaded as a computer program which may be transferred from a remote computer (e.g., a server) to a requesting computer (e.g., a client) by way of data signals embodied in a carrier wave or other propagation medium via a communication link (e.g., a modem or network connection).

Throughout the foregoing description, for the purposes of explanation, numerous specific details were set forth in order to provide a thorough understanding of the invention. It will be apparent, however, to one skilled in the art that the invention may be practiced without some of these specific details. Accordingly, the scope and spirit of the invention should be judged in terms of the claims which follow.

What is claimed is:

1. A print system comprising:
    a printhead array to apply presentation content to a substrate;
    one or more light field cameras to record image data at sections of the substrate during application of presentation content to the substrate; and
    a control unit to process the image data received from the one or more light field cameras to map out a surface of the substrate using the image data to determine the focal lengths at the sections of the substrate to generate a three-dimensional surface of the substrate to identify defect areas in the substrate.

2. The print system of claim 1 wherein the one or more light field cameras are located at strategic points along the substrate path to utilize the light-field property to derive measurements.

3. The print system of claim 2 wherein the one or more light field cameras are located immediately after the printhead array in the substrate path.

4. The print system of claim 2 wherein the one or more light field cameras are located to capture a single image on a radial surface.

5. The print system of claim 1 wherein the control unit maps out a surface of the substrate based on focal lengths of the one or more light field cameras.

6. The print system of claim 1 wherein the control unit focuses captured images from the image data and determines a degree of cockle that has occurred based on a magnitude of variance to focus an image.

7. The print system of claim 6 wherein the control unit processes the captured images to determine differences in "X" or "Y" direction defects to know whether defect issues are from steering/rollers or printing/drying.

8. The print system of claim 7 wherein the determination of differences in "X" or "Y" direction defects permits a determination as to whether a defect is due to steering/rollers problems or printing/drying problems.

9. The print system of claim 1 wherein the control unit provides dynamic feedback to a paper control system to correct defective substrate regions detected during processing the image data.

10. The print system of claim 1 wherein the control unit processes the imaging data to identify color and print quality defects recorded by the one or more light field cameras.

11. The print system of claim 10 wherein the control unit transmits one or more messages to a graphical user interface (GUI) to provide print quality defect data to an operator.

12. A print verification system comprising:
    one or more light field cameras to record image data at sections of the substrate during application of presentation content to the substrate; and
    a control unit to process the image data received from the one or more light field cameras to map out a surface of the substrate using the image data to determine the focal lengths at the sections of the substrate to generate a three-dimensional surface of the substrate to indentify defect areas in the substrate.

13. The print verification system of claim 12 wherein the control unit maps out a surface of the substrate based on focal lengths of the one or more light field cameras.

14. The print verification system of claim 12 wherein the control unit focuses captured images fro the image data and determines a degree of cockle that has occurred based on a magnitude of variance to focus an image.

15. The print verification system of claim 14 wherein the control unit processes the captured images to determine differences in "X" or "Y" direction defects to know whether defect issues are from steering/rollers or printing/drying.

16. The print verification system of claim 15 wherein the determination of differences in "X" or "Y" direction defects permits a determination as to whether a defect is due to steering/ rollers problems or printing/drying problems.

17. The print verification system of claim 12 wherein the control unit provides dynamic feedback to a paper control system to correct defective substrate regions detected during processing the image data.

18. The print verification system of claim 12 wherein the control unit processes the imaging data to identify color and print quality defects recorded by the one or more light field cameras.

19. The print verification system of claim 12, wherein the control unit captures and manages a trans-web profile of the substrate.

20. A method comprising:
   one or more light field cameras recording image data at sections of a substrate during printing to the substrate; and
   a control unit processing the image data received from the one or more light field cameras to map out a surface of the substrate using the image data to determine the focal lengths at the sections of the substrate to generate a three-dimensional surface to the substrate to identify defect areas in the substrate.

* * * * *

UNITED STATES PATENT AND TRADEMARK OFFICE
CERTIFICATE OF CORRECTION

| | | |
|---|---|---|
| PATENT NO. | : 9,132,665 B2 | Page 1 of 1 |
| APPLICATION NO. | : 13/973088 | |
| DATED | : September 15, 2015 | |
| INVENTOR(S) | : Scott Richard Johnson et al. | |

It is certified that error appears in the above-identified patent and that said Letters Patent is hereby corrected as shown below:

Claims

In column 4, at line 59 claim 14, delete, "fro" and insert -- from --.

In column 5, at line 2 claim 16, delete, "rollers," and insert -- roller --.

Signed and Sealed this
Eighth Day of March, 2016

Michelle K. Lee
*Director of the United States Patent and Trademark Office*